(12) United States Patent
Yoshimura et al.

(10) Patent No.: US 8,770,907 B2
(45) Date of Patent: Jul. 8, 2014

(54) CRYOPRESERVATION DEVICE

(75) Inventors: Shigehiro Yoshimura, Kai (JP);
Masahiro Takeuchi, Tokyo (JP);
Mamoru Fujita, Kai (JP); Hidetoshi Ohta, Koufu (JP)

(73) Assignee: Taiyo Nippon Sanso Corporation, Tokyo (JP)

( * ) Notice: Subject to any disclaimer, the term of this patent is extended or adjusted under 35 U.S.C. 154(b) by 520 days.

(21) Appl. No.: 12/812,354

(22) PCT Filed: Nov. 11, 2008

(86) PCT No.: PCT/JP2008/070495
§ 371 (c)(1),
(2), (4) Date: Jul. 9, 2010

(87) PCT Pub. No.: WO2009/090793
PCT Pub. Date: Jul. 23, 2009

(65) Prior Publication Data
US 2010/0275636 A1  Nov. 4, 2010

(30) Foreign Application Priority Data

Jan. 18, 2008 (JP) ................ P2008-009393
Oct. 17, 2008 (JP) ................ P2008-268768

(51) Int. Cl.
*F17C 13/00* (2006.01)

(52) U.S. Cl.
USPC ............. 414/225.01; 62/457.9; 220/560.12

(58) Field of Classification Search
USPC ........... 62/374, 375, 447, 457.9; 220/560.12, 220/560.14; 414/225.01
See application file for complete search history.

(56) References Cited

U.S. PATENT DOCUMENTS

| | | | | |
|---|---|---|---|---|
| 3,168,362 | A * | 2/1965 | Perkins | 312/400 |
| 3,303,667 | A * | 2/1967 | Perkins | 62/457.9 |
| 3,707,079 | A * | 12/1972 | Hawker | 62/189 |
| 4,314,450 | A * | 2/1982 | Pelloux-Gervais | 62/51.1 |
| 5,419,143 | A * | 5/1995 | Leonard et al. | 62/51.1 |
| 5,620,110 | A * | 4/1997 | Delatte | 220/560.1 |
| 6,467,642 | B2 * | 10/2002 | Mullens et al. | 220/560.1 |
| 2007/0267419 | A1 | 11/2007 | Fuhr | |

FOREIGN PATENT DOCUMENTS

| | | |
|---|---|---|
| FR | 2664156 A1 | 1/1992 |
| JP | Y-32-015770 | 12/1957 |
| JP | U-48-007581 | 2/1973 |
| JP | Y-48-010141 | 3/1973 |

(Continued)

OTHER PUBLICATIONS

International Search Report for PCT/JP2008/070495 mailed Feb. 17, 2009.

(Continued)

*Primary Examiner* — Jonathan Snelting
(74) *Attorney, Agent, or Firm* — Nixon & Vanderhye, PC

(57) ABSTRACT

A cryopreservation vessel of the present invention includes a vessel body which holds a low-temperature liquefied gas, a cap which closes an opening section of the vessel body and has a plurality of through holes that are formed so as to pass through in a vertical direction, and ampoule storing tools which are housed so as to be able to pass through the through holes of the cap, and the ampoule storing tools are each comprised of a support pillar and a plurality of ampoule storing sections which are equipped with the support pillar so as to be arrayed in a vertical direction of the support pillar.

20 Claims, 12 Drawing Sheets

(56) References Cited

FOREIGN PATENT DOCUMENTS

| JP | U-49-064467 | 6/1974 |
|---|---|---|
| JP | U-56-053701 | 5/1981 |
| JP | A-59-211446 | 11/1984 |
| JP | 1-200157 | 8/1989 |
| JP | 1-167900 | 11/1989 |
| JP | 05-060299 | 3/1993 |
| JP | 5-49294 | 6/1993 |
| JP | 6-167431 | 6/1994 |
| JP | 8-192363 | 7/1996 |
| JP | 2801809 | 7/1998 |
| JP | 3135034 | 12/2000 |
| JP | 2002-214227 | 7/2002 |
| JP | 2002-282712 | 10/2002 |
| JP | 2005-143873 | 6/2005 |
| JP | 2007-155460 | 6/2007 |
| JP | 2007-271279 | 10/2007 |
| JP | 2008-285181 | 11/2008 |

OTHER PUBLICATIONS

CD-ROM of the Specification and drawings annexed to the request of JP Utility Model Appln. No. 108611/1991 (Laid-Open No. 49294/1993), Shin-Etsu Chemical Co., Ltd., (Jun. 29, 1993).

Office Action (Notice of Allowance) and English translation issued in JP 2008-268768 on Nov. 16, 2010.

Official Action and English translation in JP 2007-130357 mailed Jan. 31, 2012.

* cited by examiner

CRYOPRESERVATION DEVICE

This application is the U.S. national phase of International Application No. PCT/JP2008/070495, filed 11 Nov. 2008, and claims priority to Japan Application No. 2008-009393, filed 18 Jan. 2008 and Japan Application No. 2008-268768, filed 17 Oct. 2008, the entire contents of each of which is hereby incorporated by reference.

TECHNICAL FIELD

The present invention relates to a glove box (i.e. a cryopreservation device) that houses a cryopreservation vessel, and particularly to a glove box that is configured to be capable of preventing frost formation onto the ampoules or the like when ampoules housed in the cryopreservation vessel are taken in and out.

Priorities are claimed on Japanese Patent Application No. 2008-009393 filed on Jan. 18, 2008 and Japanese Patent Application No. 2008-268768 filed on Oct. 17, 2008 in Japan, the contents of which are incorporated herein by reference.

BACKGROUND ART

As a method for simply storing biological samples such as spermatozoa, embryo, and cells of experimental animals used for development of new medicines or medical basic research, a cryopreservation method is generally used. In particular, a cryopreservation method using liquefied nitrogen is considered to be capable of most stably storing biological samples for a long period, and is broadly used.

In this cryopreservation method, biological samples are stored in ampoules, and the ampoules are stored in ampoule storing tools, to be frozen-stored in a cryopreservation vessel. At the time of putting an ampoule into or out of the cryopreservation vessel, the ampoule and the ampoule storing tool are exposed to the atmosphere, and moisture adheres to the ampoule, the ampoule storing tool, the cryopreservation vessel, and the like as frost. Further, when the ampoule is stored in the ampoule storing tool or when the ampoule storing tool is stored in the cryopreservation vessel, the storing work is difficult due to frost adhering to be deposited on the ampoule storing tool in some cases.

A management code is put on each of the ampoules housed in the cryopreservation vessel, to manage the ampoules. When frost adheres to an ampoule, it is difficult to read the management code addressed on the surface of the ampoule, that causes a malfunction of a read sensor.

Moreover, when frost adheres to an ampoule, dust in the atmosphere adheres thereto at the same time, that causes the contamination of the ampoule. Conventionally, in order to eliminate frost adhering to ampoules and ampoule storing tools, it has been necessary to wipe out those each time of putting-in/out.

Further, since frost adhering to ampoules and ampoule storing tools are accumulated as frost or ice particles in the cryopreservation vessel each time of putting-in/out, in the case of eliminating those, it has been necessary to periodically do so-called maintenance that, after stored samples such as the ampoules in the cryopreservation vessel are moved, the liquid nitrogen in the vessel is removed and the inside of the vessel is dried.

Further, in the case where identification of an ampoule storing tool or an ampoule is performed by visual confirmation of an operator, there have been the problems of confusion, missing, and the like of ampoules due to adhesion of frost.

As a conventional technology with respect to a glove box, there are the following technologies for example.
[Patent Document 1] Japanese Unexamined Patent Application, First Publication No. Hei 8-192363
[Patent Document 2] Japanese Patent No, 2,801,809
[Patent Document 3] Japanese Patent No. 3,135,034
[Patent Document 4] Japanese Unexamined Utility Model Application, First Publication No. Hei 5-49294
[Patent Document 5] Japanese Unexamined Patent Application, First Publication No. Hei 1-200157
[Patent Document 6] Japanese Unexamined Patent Application, First Publication No. 2002-282712

DISCLOSURE OF INVENTION

Problems to be Solved by the Invention

Accordingly, it is an object of the present invention to provide a glove box in which it is possible to restrain frost from adhering to those and the cryopreservation vessel at the time of putting an ampoule and an ampoule storing tool into and out of a cryopreservation vessel, which does not cause confusing, missing, and the like of ampoules. Further, it is another object of the present invention to provide a cryopreservation vessel suitable for such a glove box.

Means to Solve the Problems

In order to solve such a problem,
a cryopreservation vessel according to a first aspect of the present invention includes a vessel body which holds a low-temperature liquefied gas; a cap which closes an opening section of the vessel body and has a plurality of through holes that are formed so as to pass through in a vertical direction; and ampoule storing tools which are housed so as to be able to pass through the through holes of the cap, wherein the ampoule storing tools are each comprised of a support pillar and a plurality of ampoule storing sections which are equipped with the support pillar so as to be arrayed in a vertical direction of the support pillar.

In the first aspect of the present invention, it is preferable that the cryopreservation vessel further includes sheath tubes which be inserted into the through holes of the cap, wherein the ampoule storing tools are housed so as to be able to pass through the sheath tubes, and a plurality of gas permeable holes are formed in each of the sheath tubes.

In other words, it is preferable that the cryopreservation vessel according to the first aspect of the present invention include a vessel body which holds a low-temperature liquefied gas; a cap which closes an opening section of the vessel body and has a plurality of through holes that are formed so as to pass through in a vertical direction; sheath tubes which are inserted into the through holes of the cap; and ampoule storing tools which are housed so as to be able to pass through the sheath tubes, wherein a plurality of gas permeable holes are formed in each of the sheath tubes, and the ampoule storing tools are each comprised of a support pillar and a plurality of ampoule storing sections which are equipped with the support pillar so as to be arrayed in a vertical direction of the support pillar.

A glove box according to a second aspect of the present invention includes a housing section which houses the cryopreservation vessel; and a putting-in/out work space section which is provided so as to be communicated with an upper portion of the housing section, wherein the putting-in/out work space section is transparently visible from outside, and is filled with a dry gas to be at positive pressure, and a putting-in/out work for an ampoule storing tool of the cryopreservation vessel housed in the housing section is performed inside the putting-in/out work space section.

In the glove box according to the second aspect of the present invention, it is preferable that a gas exhaust port equipped with a back-flow prevention mechanism or a filter be provided in a wall surface of the putting-in/out work space section, and ampoule exit/entrance boxes be provided in a wall surface of the housing section.

Further, in the glove box according to the second aspect of the present invention, it is preferable that a dew point meter for measuring a dew point in the putting-in/out work space section be provided, and a dry gas supply section, which supplies a dry gas for lowering the dew point in the space section into the putting-in/out work space section in the case where a value indicated by the dew point meter shows a predetermined value or more, be provided.

Further, in the glove box according to the second aspect of the present invention, it is preferable that an automatic handling robot, which pulls up a specified ampoule storing tool from the cryopreservation vessel, and next pushes the specified ampoule storing tool, be provided at a ceiling portion of the putting-in/out work space section.

Further, in the glove box according to the second aspect of the present invention it is preferable that the automatic handling robot operate by three-axial control on the basis of instructions on a position of a specified ampoule storing tool and a position of an ampoule stored in the ampoule storing tool.

Further, in the glove box according to the second aspect of the present invention, it is preferable that the automatic handling robot be equipped with a gripper head, and the gripper head travel in three-axis directions to move to a position of a specified ampoule storing tool, pull up the ampoule storing tool until a specified ampoule is exposed from the cryopreservation vessel, and next push the ampoule storing tool.

Further, in the glove box according to the second aspect of the present invention, it is preferable that a pass box be provided to the putting-in/out work space section, the pass box have an airtight operation port that opens outside, and have an upper housing pipe into which an ampoule storing tool pulled up from the cryopreservation vessel by the automatic handling robot is inserted, and a takeoff port for taking out an ampoule from the inserted ampoule storing tool be formed in the upper housing pipe.

Further, in the glove box according to the second aspect of the present invention, it is preferable that a pass box be provided to the putting-in/out work space section, the pass box have an airtight operation port that opens outside, and have a back surface in which a longitudinal groove portion is formed such that an ampoule storing tool pulled up from the cryopreservation vessel by the automatic handling robot be set along the longitudinal groove portion, and a takeoff port for taking out an ampoule from the inserted ampoule storing tool be formed in the longitudinal groove portion.

Further, in the glove box according to the second aspect of the present invention, it is preferable that the pass box be made of a transparent material, and the inside of the pass box be filled with a dry gas.

Further, in the glove box according to the second aspect of the present invention, it is preferable that a bar-code be put on the ampoule, and the ampoule of the ampoule storing tool taken out by the automatic handling robot be identified on the basis of identification management information of the bar-code.

Further, in the glove box according to the second aspect of the present invention, it is preferable that a tube line for supplying a liquefied gas to the cryopreservation vessel be provided, and the tube line pass through the housing section and the cryopreservation vessel, and one end of the tube line extend to a bottom portion of the cryopreservation vessel and the other end be connected to a liquefied gas supplier.

Effect of the Invention

According to the present invention, since the putting-in/out work space section is filled with a dry gas, the inside of the putting-in/out work space section can be kept in a dry state. Further, it is possible to restrain frost from adhering to those and the cryopreservation vessel at the time of putting an ampoule and an ampoule storing tool into and out of a cryopreservation vessel. Therefore, it is possible to easily perform reading of sample management codes addressed on the surface of an ampoule, and reduce the frequency of maintenances for the cryopreservation vessel.

Moreover, since the putting-in/out work space section is filled with a dry gas to be at positive pressure, the atmosphere is prevented from invading, and the atmosphere containing dust, bacteria, viruses, and the like, and exhaled air of a worker are restrained from mixing into the putting-in/out work space section. Further, the putting-in/out work space section can be kept in a dry state and a clean state, which makes it possible to prevent contamination of ampoules.

Further, since the humidity in the putting-in/out work space section is monitored by a dew point meter, and a dry gas is introduced into the putting-in/out work space section in the case where a dew point rises, the inside of the putting-in/out work space section is always kept in a dry state, which makes it possible to certainly prevent front formation.

According to the glove box in which the automatic handling robot is installed at the ceiling portion of the putting-in/out work space section, it is possible to automatically perform the work that a specified ampoule storing tool is pulled up from the cryopreservation vessel, and an ampoule stored in the ampoule storing tool is exposed from the cryopreservation vessel. Further, it is possible to efficiently carry out taking-out and reception of a specified ampoule from the cryopreservation vessel.

Further, according to the glove box in which the pass box is provided to the putting-in/out work space section, and the ampoule storing tools are brought into the pass box, it is possible to perform in taking-out and receiving works for ampoules and the like without wearing gloves, which improves the work efficiency.

Moreover, provided that a bar-code is put on each ampoule, and an operation of the automatic handling robot is controlled on the basis of identification management information of the bar-code, it is possible for the automatic handling robot to take out a target ampoule storing tool from the cryopreservation vessel, to locate the target ampoule at the takeoff port of the pass box. Further, since it is possible to read the bar-code of the ampoule with a bar-code reader to identify the ampoule, ampoules are not confused in any case, which makes it possible to certainly put in/out each ampoule.

By use of a cryopreservation vessel including a vessel body, a cap which closes an opening section of the vessel body, and in which a plurality of through holes are formed, and ampoule storing tools which are housed so as to be able to pass through the cap, and the ampoule storing tools each have a plurality of ampoule storing sections, the number of times of taking out ampoules other than target ampoules to the outside of the cryopreservation vessel is greatly decreased in the putting-in/out work. Further, thereby further reducing the frequency of frost formations onto the ampoules and the like.

DESCRIPTION OF THE REFERENCE SYMBOLS

Figure 1:
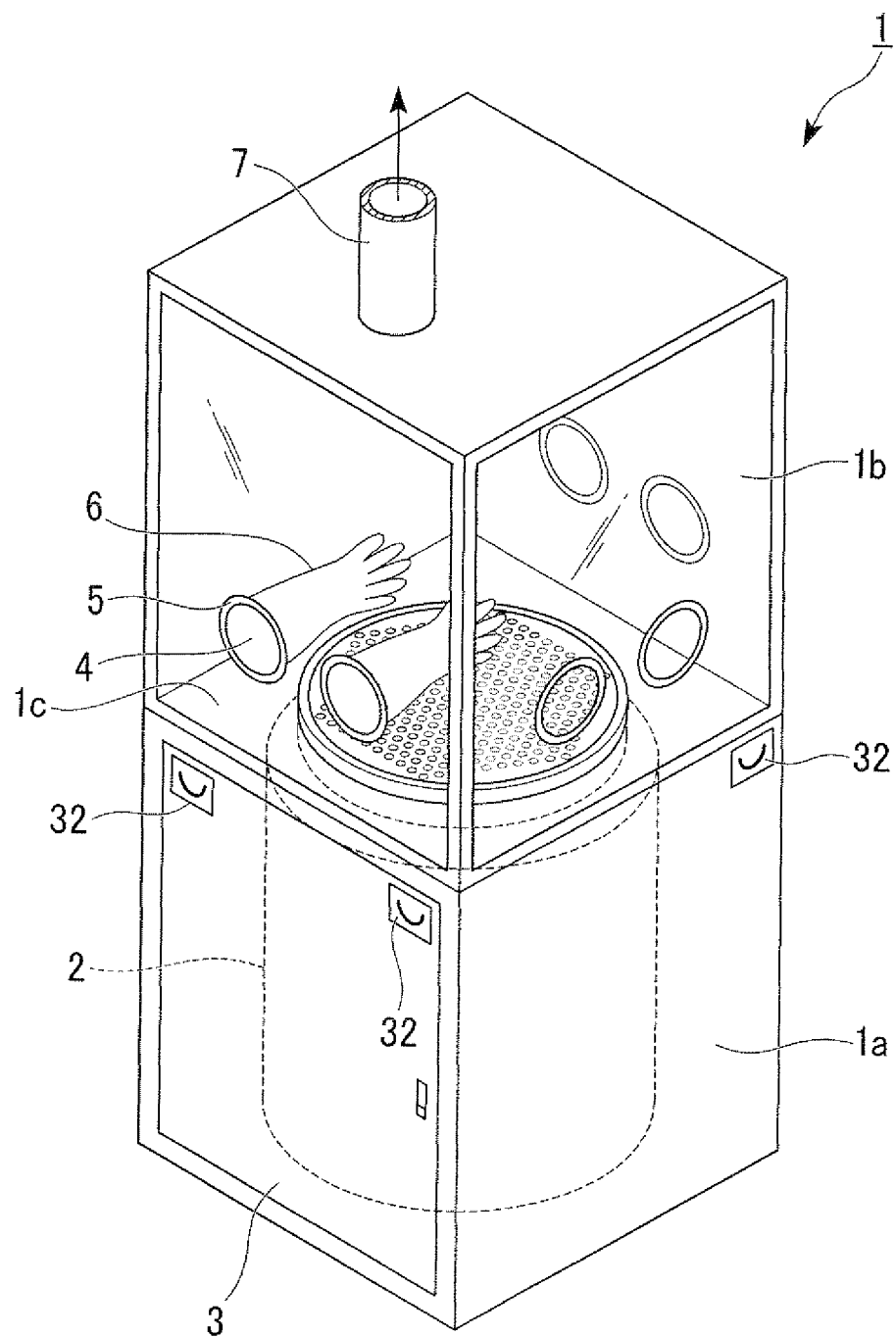
FIG. 1 is an entire schematic block diagram showing an example of a glove box of the present invention.

1 Glove box
1a Housing section
1b Putting-in/out work space section
2 Cryopreservation vessel
7 Exhaust port
8 Vessel body
9 Cap
10 Ampoule storing tool
11 Sheath tube
20 Support pillar
23 Ampoule storing section
27 Dew point meter
31 Liquefied gas supply pipe
32 Ampoule exit/entrance box
41 Liquefied gas supply source
58 Gripper head
71 Pass box
72 Operation port
76 Upper housing pipe
77 Takeoff port
79 Bar-code reader
82 Clamp

BEST MODE FOR CARRYING OUT THE INVENTION

Hereinafter, an embodiment of the present invention will be described with reference to FIGS. 1 to 7.
(Glove Box)

FIG. 1 is a schematic block diagram showing an example of a glove box 1 of the present invention. The glove box 1, in this example is a rectangular parallelepiped box whose outside dimension is approximately 2,000 mm high, 1,000 mm wide, and 1,000 mm deep.

This glove box 1 is in a vertical direction divided into two with a partition board 1c, that is comprised of a putting-in/out work space section (hereinafter referred as to a work space section) 1b in the upper portion and a housing section 1a in the lower portion. The sizes and shapes of the housing section 1a and the work space section 1b are respectively cubes of approximately 1,000 mm on a side.

A cryopreservation vessel 2 can be housed in the housing section 1a, and a circular through hole is formed in the center of the partition board 1c, and the glove box 1 is configured to be capable of approaching the opening portion of the cryopreservation vessel 2 in the housing section 1a via the through hole from the work space section 1b.

The cryopreservation vessel 2 can be taken into and out of the housing section 1a by opening and closing a door 3 formed on one side surface of the housing section 1a. The opening portion of the cryopreservation vessel 2 built in the housing section 1a faces the work space section 1b to be communicated with the work space section 1b, and it is possible to take into and out an ampoule storing tool through the opening portion.

Ampoule exit/entrance boxes 32 are formed in the outer wall surfaces of the housing section 1a.

Figure 2:
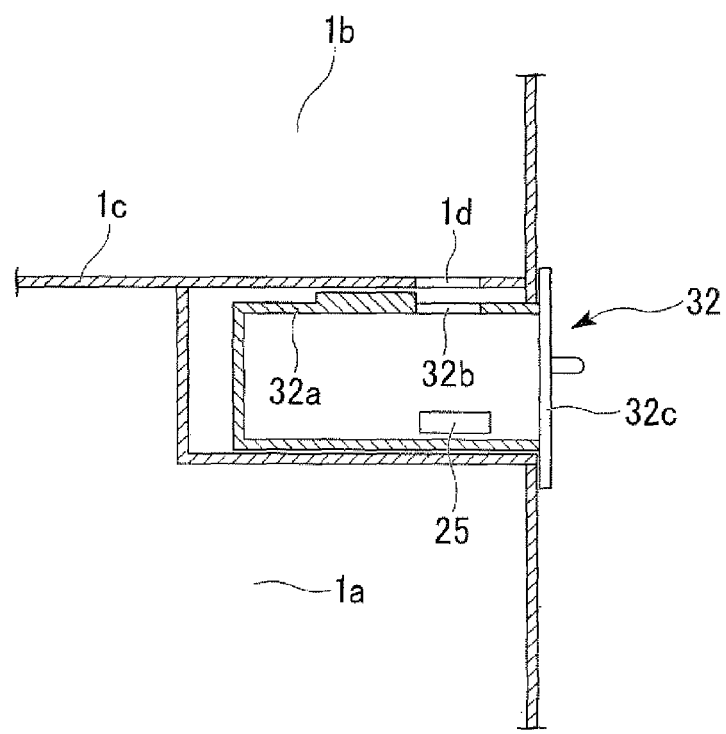
FIG. 2 is a schematic cross sectional diagram showing an example of an ampoule exit/entrance box in the glove box of the present invention.

The ampoule exit/entrance boxes 32 are for temporarily housing ampoules taken out of the cryopreservation vessel 2 or ampoules to be housed in the cryopreservation vessel 2, and the ampoule exit/entrance boxes 32 are communicated with openings 1d formed in the partition board 1c (refer to FIG. 2).

FIG. 2 shows an example of the ampoule exit/entrance box 32. The ampoule exit/entrance boxes 32 are located to be provided immediately beneath the partition board 1c at positions corresponding to the four corners of the partition board 1c, so as to skirt around a circular vessel body 8 of the cryopreservation vessel 2.

The ampoule exit/entrance box 32 is an usual drawer with a lid 32a, and an opening 32b for dropping an ampoule 25 into the box is formed in the lid 32a. This opening 32b is to be communicated with the opening 1d formed in the partition board 1c at the time of pushing in the ampoule exit/entrance box 32.

When the ampoule exit/entrance box 32 is pushed into the back, the opening portion formed in the outer wall of the housing section 1a is closed to be airtight with a front plate 32c of the ampoule exit/entrance box 32. Further, when the ampoule exit/entrance box 32 is drawn out to the front side, the opening 1d formed in the partition board 1c is closed to be airtight with the lid 32a. With such a structure, the external air is prevented from invading the inside of the work space section 1b in accordance with a time of taking in or out an ampoule.

The work space section 1b is formed by covering its periphery with transparent plates comprised of glass or acrylic resin, and is configured to be capable of visually confirming a work in the work space section 1*b* from the outside. For example, the front surface and the both side surfaces of the work space section 1*b* are covered with acrylic resin plates or the like. Further, the acrylic resin plates covering the periphery of the work space section 1*b* may be doubled to have thermal insulating properties, to prevent dew condensation and frost formation on the outer surfaces of the acrylic resin plates.

On the three surfaces of the front surface, one side plate, and the opposite side plate, which are the transparent plates covering the work space section 1*b*, round-shaped glove mounting opening portions 4 are formed in two places for each surface. Glove mounting frames 5 made of rubber are mounted to the opening portions 4, and gloves 6 made of rubber are mounted to the glove mounting frames 5.

The opening portions 4 are provided at positions of 1,300 to 1,400 mm from the floor in order for an operator in a standing operating state to be able to smoothly perform putting-in/out works in the gloves 6. Note that FIG. 1 shows a state in which the gloves 6 are mounted to the opening portions 4 formed in the one side plate surface.

Due to the fact that the gloves 6 are provided in the above-described three surfaces of the work space section 1*b*, it is possible to perform works with respect to the inside of the work space section 1*b* from the three directions. Therefore, even when ampoule storing tools 10 are disposed entirely in the opening portion of the cryopreservation vessel 2, it is possible to easily perform putting-in/out works by use of the gloves 6 formed in one of the three surfaces.

An exhaust port 7 is formed in the ceiling wall of the work space section 1*b*, and a back-flow prevention mechanism or a filter (not shown) is mounted thereto, to prevent dust in the atmosphere from invading the work space section 1*b*.

Figure 3:
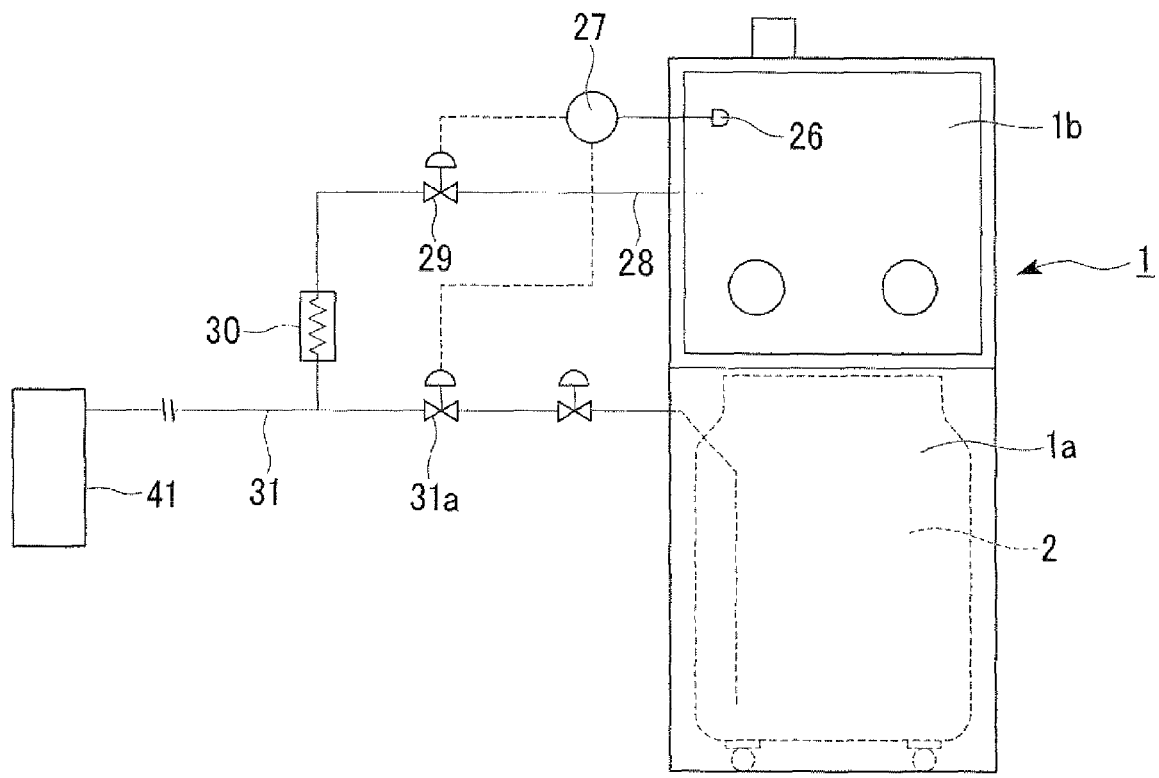
FIG. 3 is a schematic block diagram showing an example of dry gas supply equipment in the glove box of the present invention.

Further, as shown in FIG. 3, a dew point sensor 26 is mounted in the work space section 1*b*. This dew point sensor 26 is to measure a moisture content in the ambient gas in the work space section 1*b*, and a signal from the dew point sensor 26 is transmitted to a dew point meter 27, and a dew point in the work space section 1*b* is calculated on the basis of a measured moisture content by the dew point meter 27.

In the dew point meter 27, a dew point in the work space section 1*b* is set in advance to −50° C. or the like for example, and the system is configured such that, when a dew point calculated by the dew point meter 27 is the set dew point or more, a dry gas is supplied into the work space section 1*b* from a dry gas supply tube 28.

One end of the dry gas supply tube 28 opens into the work space section 1*b*, and the other end thereof is connected to a liquefied gas supply tube 31 which will be described later, via a flow regulating valve 29 and an evaporator 30.

The flow regulating valve 29 controls a flow rate of the dry gas on the basis of a control signal from the dew point meter 27.

A low-temperature liquefied gas branched to flow from the liquefied gas supply tube 31 is evaporated by the evaporator 30 to be a dry gas, and its flow rate is controlled by the flow regulating valve 29 to be introduced into the work space section 1*b*.

(Cryopreservation Vessel)

Figure 4:
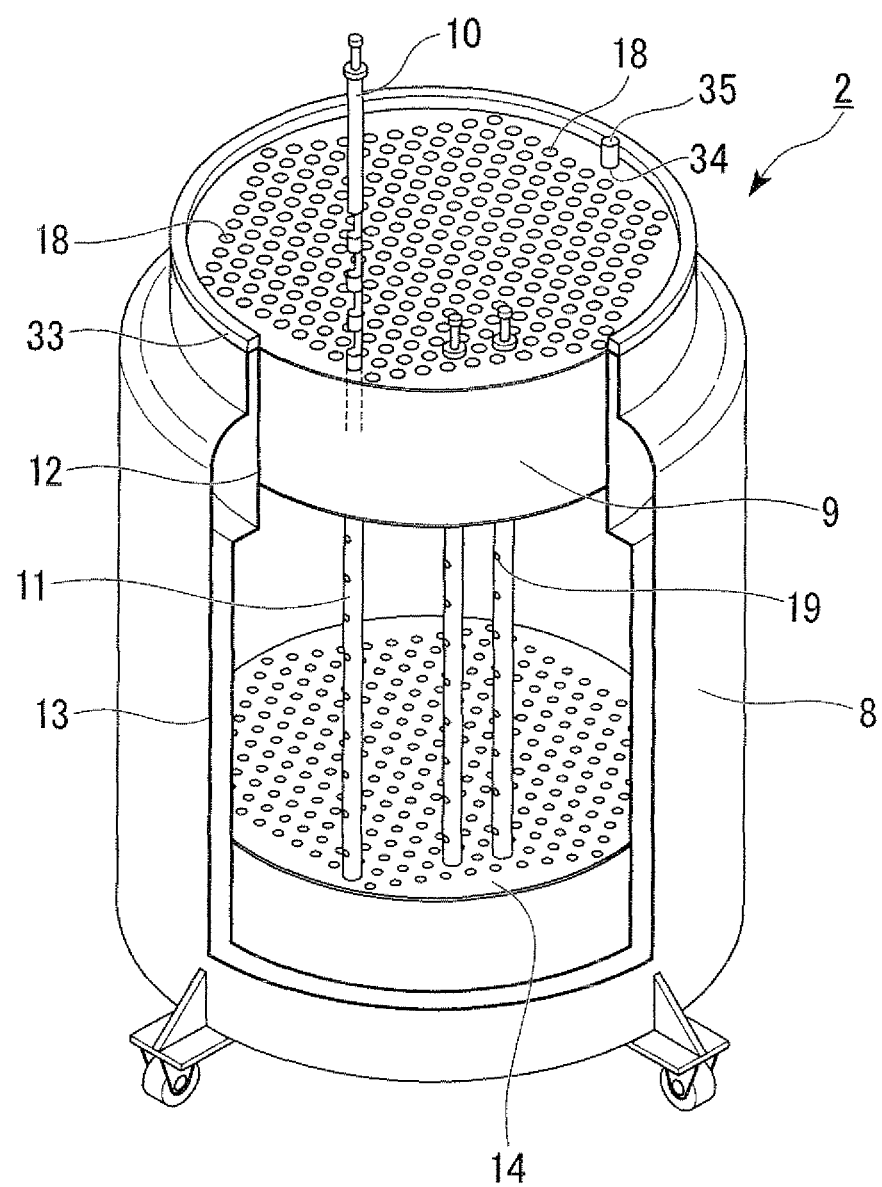
FIG. 4 is a schematic perspective view showing an example of a cryopreservation vessel, which is partially cut out, in the glove box of the present invention.

As shown in FIG. 4, the cryopreservation vessel 2 is schematically comprised of the vessel body 8, a cap 9, the ampoule storing tools 10, and sheath tubes 11. The cryopreservation vessel 2 has a double structure formed of an inner vessel 12 and an outer vessel 13 made of stainless steel or the like, and is a vacuum thermal insulating vessel in which a gap between the inner vessel 12 and the outer vessel 13 is vacuum.

A perforated plate 14 is mounted in the vicinity of the bottom portion of the inner vessel 12 of the case body 8, and the inner vessel 12 is to be filled close to the perforated plate 14 with a low-temperature liquefied gas such as liquefied nitrogen. The opening diameter of the opening section of the inner vessel 12 is made slightly smaller than the inner diameter of the body portion of the inner vessel 12, and the inner vessel 12 is formed into a so-called waistless pan shape.

Figure 5:
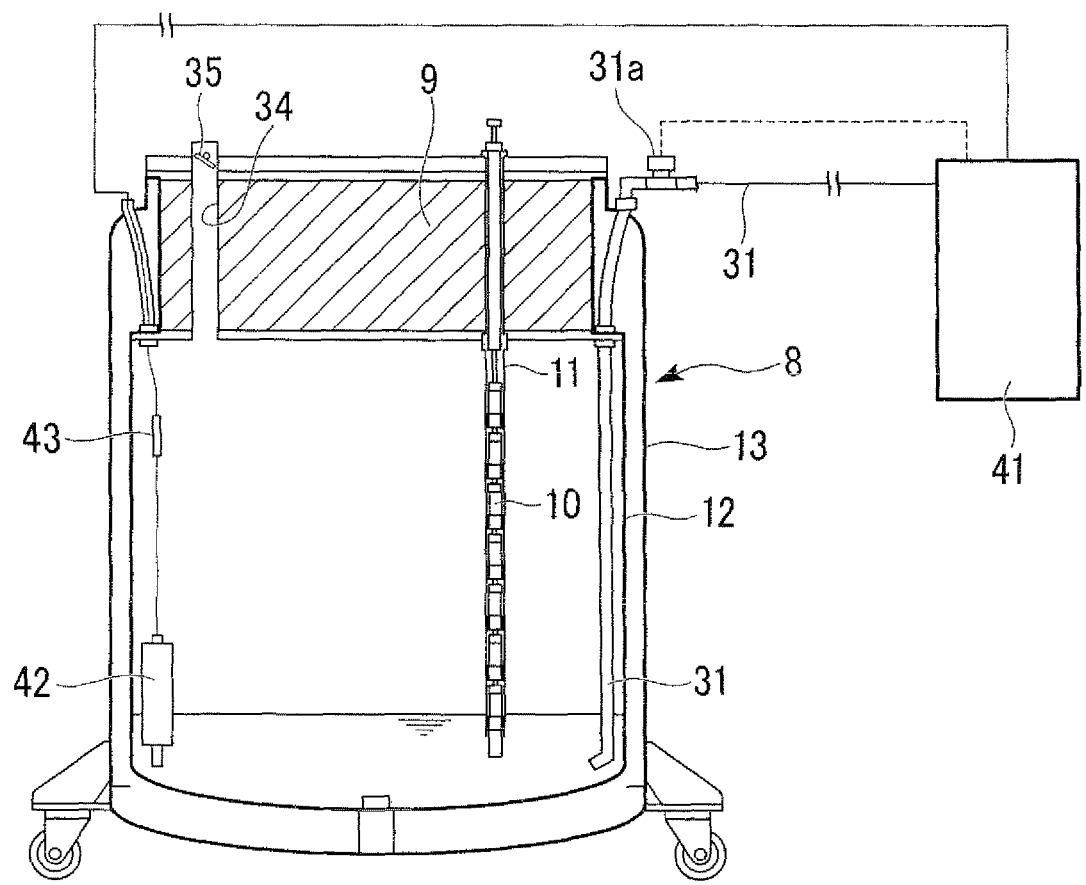
FIG. 5 is a schematic block diagram showing an example of equipment for supplying a low-temperature liquefied gas to the cryopreservation vessel in the glove box of the present invention.

Further, as shown in FIG. 5, a liquefied gas supply tube 31 for supplying or supplementing a low-temperature liquefied gas into the case body 8 is provided to the cryopreservation vessel 2. One end of the liquefied gas supply tube 31 passes through the side wall portion of the housing section 1*a* of the glove box 1 and the side wall portion of the case body 8, to extend close to the bottom portion of the inner vessel 12, and the other end thereof is connected to a liquefied gas supply source 41 via the flow regulating valve 31*a*.

Moreover, a fluid level sensor 42 sensing a trapped fluid level of a low-temperature liquefied gas, and a temperature sensor 43 sensing a temperature of a vapor phase in the vessel body 8 are provided in the vessel body 8 of the cryopreservation vessel 2. Detection signals from these sensors 42, 43 are transmitted to the liquefied gas supply source 41, to control a point of supply time and an amount supplied of a low-temperature liquefied gas to be supplied into the vessel body 8.

Figure 6:
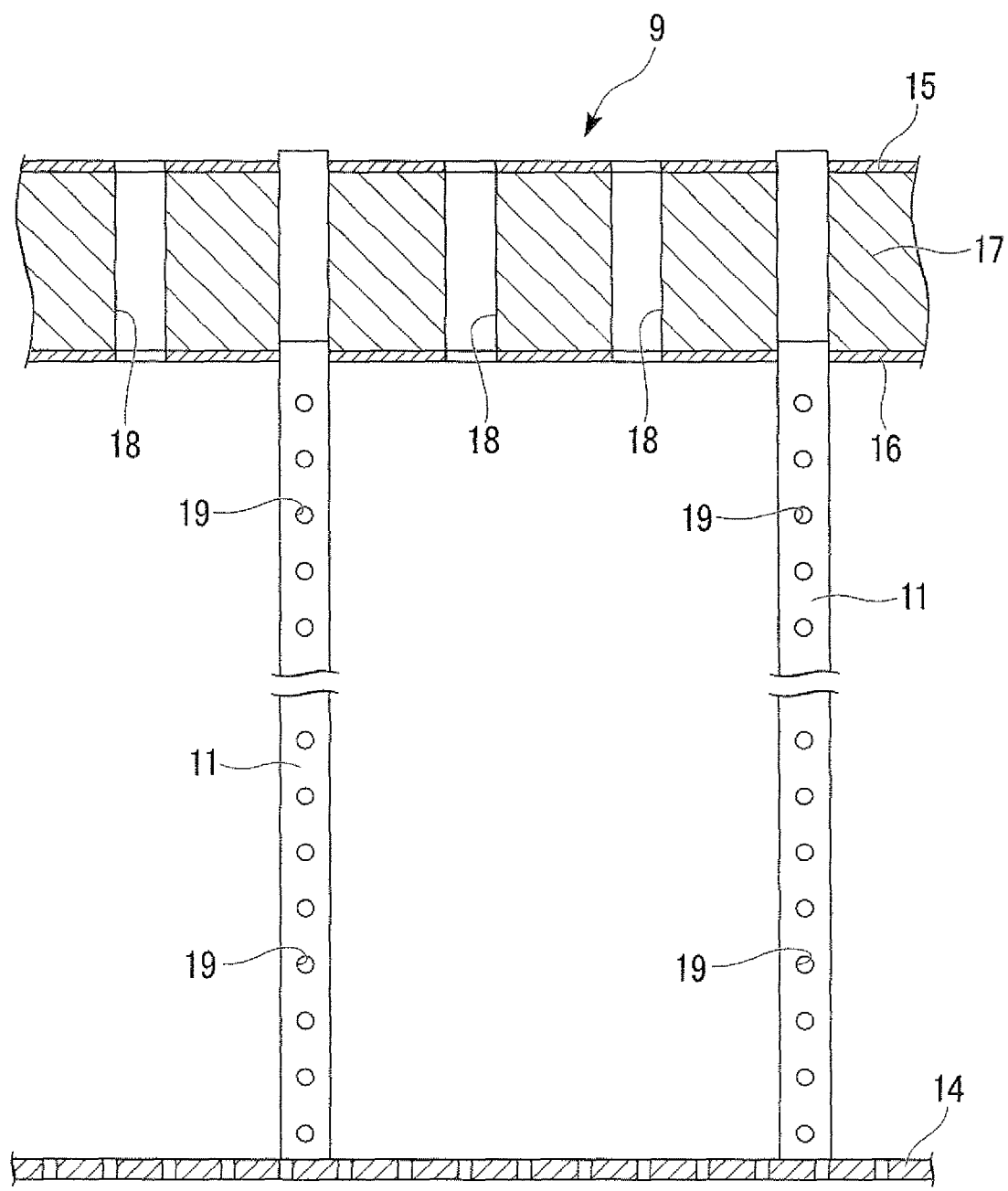
FIG. 6 is a schematic cross sectional diagram showing an example of a cap and sheath tubes in the glove box of the present invention.

The opening section of the inner vessel 12 of the vessel body 8 is configured to be closed so as to be openable and closable with the cap 9. As shown in FIG. 4, the cap 9 has a columnar shape whose outer diameter is approximately the same as the opening diameter of the opening section of the inner vessel 12. As shown in FIG. 6, the cap 9 is comprised of disk-shaped upper board 15 and lower board 16, and a thermal insulating body 17 made of a thermal insulating material such as an urethane resin foam therebetween, to have a thickness of approximately 200 to 300 mm, that is high in thermal insulation performance.

A large number of, for example, 300 to 500 insertion holes 18 passing through the cap 9 in its thickness direction (in a vertical direction) are formed in the cap 9. An inner diameter of the insertion hole 18 is set to approximately 15 to 25 mm.

The cap is configured such that the sheath tubes 11 are inserted into all these insertion holes 18. As shown in FIG. 4, the sheath tube 11 has a straight tube shape with an outer diameter of 15 to 25 mm, an inner diameter of 13 to 23 mm, and a length of 500 to 700 mm approximately, and the bottom portion thereof reaches the perforated plate 14, and the opening section thereof opens so as to be exposed on the upper side surface of the cap 9.

Portions of the sheath tubes 11 touching the cap 9 are comprised of resin pipes, and portions lower than those are comprised of stainless steel, aluminum alloy, or the like.

Further, a large number of small diameter gas permeable holes 19 are formed in the peripheral walls of the sheath tubes 11.

A fixing claw (not shown) for fixing the sheath tube 11 to the cap 9 is integrally mounted to the top portion of the sheath tube 11, and the fixing claw is engaged with an engaging concave portion (not shown) formed in the upper edge (the upper board 15) of the insertion hole 18 of the cap 9, to fix the sheath tube 11 to the cap 9, which causes the sheath tube 11 to be not pulled up at the same time of pulling up the ampoule storing tool 10.

(Ampoule Storing Tool)

Figure 7:
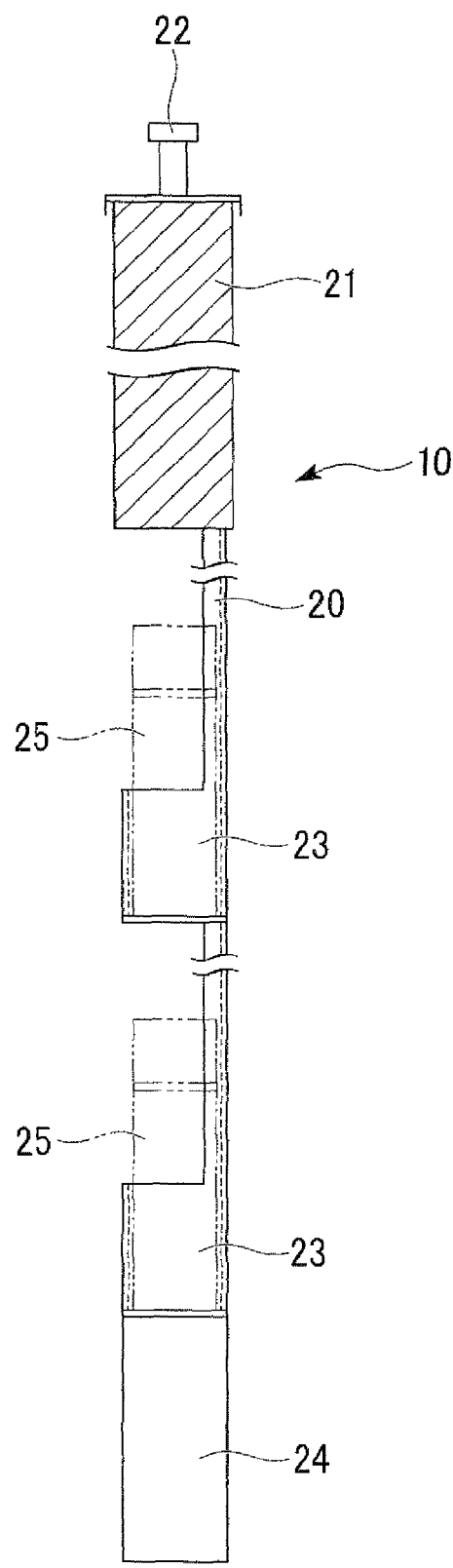
FIG. 7 is a schematic explanatory diagram showing an example of an ampoule storing tool in the glove box of the present invention.

The ampoule storing tools 10 pass through in a movable manner in a vertical direction in the sheath tubes 11. As shown in FIG. 7, the ampoule storing tool 10 is comprised of a support pillar 20 made of stainless steel, aluminum alloy, or the like, a round-bar thermal insulating section 21 provided in the upper portion of the support pillar 20, a handle portion 22 mounted to the upper portion of the thermal insulating section 21, and a plurality of, for example, eight ampoule storing sections 23 which are arrayed with intervals in a vertical direction of the support pillar 20.

The support pillar 20 has a band shape whose horizontal cross sectional shape is curved to be a circular arc shape, and a guide pipe 24 is provided to the lower end part thereof. This guide pipe 24 is for preventing the ampoule storing tool 10 from going off from the cap 9 even when the ampoule storing tool 10 is pulled up to the ampoule storing section 23 on the lowermost end. Note that the guide pipe 24 is not necessarily required.

The thermal insulating section 21 is formed such that its outer diameter is substantially the same as the inner diameter of the sheath tube 11, and the length thereof in a vertical direction is substantially the same as the thickness in a vertical direction of the cap 9.

The thermal insulating section 21 is configured such that its interior is made of a synthetic resin such as a glass fiber reinforced epoxy resin, and its peripheral portion is formed of a resin foam such as a urethane resin foam, that is high in thermal insulation performance.

As shown in FIG. 7, the support pillar 20 is not located on the central axis of the thermal insulating section, and the support pillar 20 is provided to be continued to the side portion of the thermal insulating section 21.

The ampoule storing section 23 has a bottomed cylindrical cup shape in which one ampoule 25 in which a sample to be frozen-stored is encapsulated is held and housed, and is integrally provided with the side portion of the support pillar 20. The intervals in the vertical direction of the ampoule storing section 23, are determined so as to generate a gap of approximately 5 to 10 mm between the top portion of the ampoule 25 and the bottom portion of the ampoule storing section 23 thereabove when the ampoule 25 is stored in the ampoule storing section 23.

Further, the ampoule storing section 23 is configured such that its outer diameter is slightly smaller than the outer diameter of the thermal insulating section 21, and is mounted to the support pillar 20 such that its central axis is substantially matched to the central axis of the thermal insulating section 21.

Further, as shown in FIG. 4, a ring-shaped gasket 33 comprised of a cushioning material such as a sponge or rubber is fixed to the upper end portion of the vessel body 8 of the cryopreservation vessel 2, and when the cryopreservation vessel 2 is housed at a predetermined position of the housing section 1a, the gasket 33 is pressed against the lower surface of the partition board 1c.

When the cryopreservation vessel 2 is housed in the housing section 1a, the door of the housing section 1a is opened to draw out a tray (not shown) stored in the housing section 1a, and the cryopreservation vessel 2 is placed on the tray to be pushed in the inside thereof. When the cryopreservation vessel 2 reaches the predetermined position, the cryopreservation vessel 2 is to be fixed so as to be slightly pulled upward, thereby causing the gasket 33 to come into firmly contact with the lower surface of the partition board 1c.

As shown in FIG. 4, a gas venting pipe 34 is provided to pass through the peripheral edge of the cap 9 of the cryopreservation vessel 2, and a gas venting valve 35 is mounted to the upper portion of the gas venting pipe 34, thereby, it is possible to extract a low-temperature liquefied gas evaporated in the vessel body 8 from the inside of the vessel body 8, to be capable of maintaining the inside of the vessel body 8 not to be at negative pressure.

The inside of the inner vessel 12 of the vessel body 8 is filled with a low-temperature gas that some of the low-temperature liquefied gas is evaporated as described above, and the low-temperature gas passes through the gas permeable holes 19 of the sheath tube 11 to reach the ampoule storing tool 10, to cool down the ampoule 25 held in the ampoule storing tool 10, which is brought into a frozen state.

Thereby, it is possible to store the large number of ampoules 25 in a frozen state, to frozen-store them.

Note that the ampoule 25 to be housed in the cryopreservation vessel 2 is generally an ampoule in a prior-frozen state. However, the ampoule 25 may be an ampoule in another state.

In the cryopreservation vessel 2 having such a structure, a large number of the ampoules 25 can be housed in one cryopreservation vessel 2 as compared with the conventional technology. Further, since the number of ampoules to be housed in each of the ampoule storing tools 10, the number of times of taking out the ampoules 25 to the outside of the cryopreservation vessel 2 at the time of putting-in/out works is greatly decreased, which brings about the advantage that the frequency of frost formations onto the ampoules is reduced.

(Usage of Glove Box)

Next, the usage of the glove box 1 having such a structure will be described.

First, the inside of the inner vessel 12 of the vessel body 8 is filled close to the perforated plate 14 with a low-temperature liquefied gas such as liquefied nitrogen.

Next, the opening portion of the cryopreservation vessel 2 is closed with the cap 9, and the sheath tubes 11 are inserted into all the insertion holes 18 of the cap 9.

Next, a dry gas such as a nitrogen gas is introduced into the inside of the work space section 1b from the dry gas supply tube 28, to set pressure inside the work space section 1b to positive pressure which is higher by 0.1 to 10% than the external air pressure, which prevents the external air from invading into the glove box 1.

Examples of a method for supplying a dry gas into the work space section 1b include a method for supplying a dry gas through the dry gas supply pipe 28 as described above, and a method for supplying a low-temperature liquefied gas evaporated from the cryopreservation vessel 2 via the gas venting pipe 34, which is provided in the cap 9 of the cryopreservation vessel 2, into the work space section 1b.

The dry gas in the work space section 1b is exhausted from the exhaust port 7 as needed. Since the filter and the back-flow prevention mechanism are provided to the exhaust port 7, although the dry gas is made to flow from the inside of the work space section 1b to the outside of the work space section 1b, the dry gas does not flow from the outside of the work space section 1b to the inside of the work space section 1b in any case.

Thereby, bringing about a state in which the inside of the work space section 1b is always filled with the dry gas.

In the case where the ampoule 25 is housed in the cryopreservation vessel 2, the ampoule 25 in which a sample to be frozen-stored is encapsulated is put into the ampoule exit/entrance box 32, to be carried into the work space section 1b. Next, an operator pulls up the predetermined ampoule storing tool 10 from the cryopreservation vessel 2 while inserting his/her hands into the gloves 6, 6 of the glove box 1. Thereafter, after the ampoule 25 in the ampoule exit/entrance box 32 is taken out, to be housed in the ampoule storing section 23 of the predetermined ampoule storing tool 10, the ampoule storing tool 10 is pushed into the cryopreservation vessel 2.

The procedure of a work for taking out the ampoule 25 from the cryopreservation vessel 2 is inversed to that of a work for housing the ampoule 25.

Here, provided that first identification codes (for example, 1, 2, 3, . . . , and n) are respectively put on the handle portions 22 which are exposed on the surface of the cap 9 of the respective ampoule storing tools 10, or the sheath tubes 11 into which the ampoule storing tools 10 are inserted, the number of the ampoules 25 to be housed in each of the ampoule storing tools 10 is set to 8, and second identification codes of A, B, C, . . . , and H are put on the eight ampoules 25 in descending order, it is possible to identify to manage one of the ampoules 25 on the basis of an identification management number of, for example, "2-B".

Further, it is possible to recognize the ampoule storing tool 10 which stores the target ampoule 25 from the outside of the cryopreservation vessel 2.

Then, for example, in the case where the ampoule 25 with the identification management number of "2-B" is taken out of the cryopreservation vessel, after the ampoule storing tool 10 on which the first identification code "2" is put is visually confirmed from the outside of the cryopreservation vessel 2, this is pulled up from the sheath tube 11, and the ampoule 25 second from the top (the second identification code "B") is taken out. The position to which the ampoule storing tool 10 is pulled up in this case is naturally sufficient a position at which the ampoule 25 second from the top can be taken out at a maximum, and the third or lower ampoules 25 are not exposed to the external air in any case.

Further, this is the same as in the case where another one of the ampoules 25 is newly stored in the empty ampoule storing section 23 of the ampoule storing tool 10.

In case that the ampoule 25 drops off from the ampoule storing section 23 of the ampoule storing tool 10, the ampoule 25 stays in the sheath tube 11, and in this case, it is possible to collect the ampoule 25 from the sheath tube 11, which does not waste an precious sample in any case.

Further, since there is no need detach the cap 9 from the cryopreservation vessel 2 at the time of pulling up and inserting the ampoule storing tool 10, it is possible to reduce the consumption of a low-temperature liquefied gas.

In the embodiment described above, the embodiment using the sheath tube 11 has been shown. Meanwhile, in the present invention, the embodiment may not use the sheath tube 11. In this case, except for the point that it is difficult to collect the ampoule 25 which has dropped off from the ampoule storing section 23 of the ampoule storing tool 10, the same advantageous effect as in the above-described embodiment can be obtained.

Moreover, it goes without saying that there is no disadvantage even in the case of the cryopreservation vessel 2 to which the perforated plate 14 is not mounted.

Further, the shape of the ampoule storing section 23 of the ampoule storing tool 10 is not limited to the above-described shape. For example, the ampoule storing section 23 of the ampoule storing tool 10 may be configured such that two locking claw pieces are extended from the both sides of the support pillar 20, and the ampoule 25 is taken to be held with the two locking claw pieces.

Hereinafter, another embodiment of the present invention will be described with reference to FIGS. 8 to 14.

One Embodiment of Glove Box Equipped with Automatic Handling Robot

The ampoule putting-in/out work can be performed by, not only a manual operation by use of the gloves 6, but also a semi-automatic operation by use of an automatic handling robot.

Figure 8:
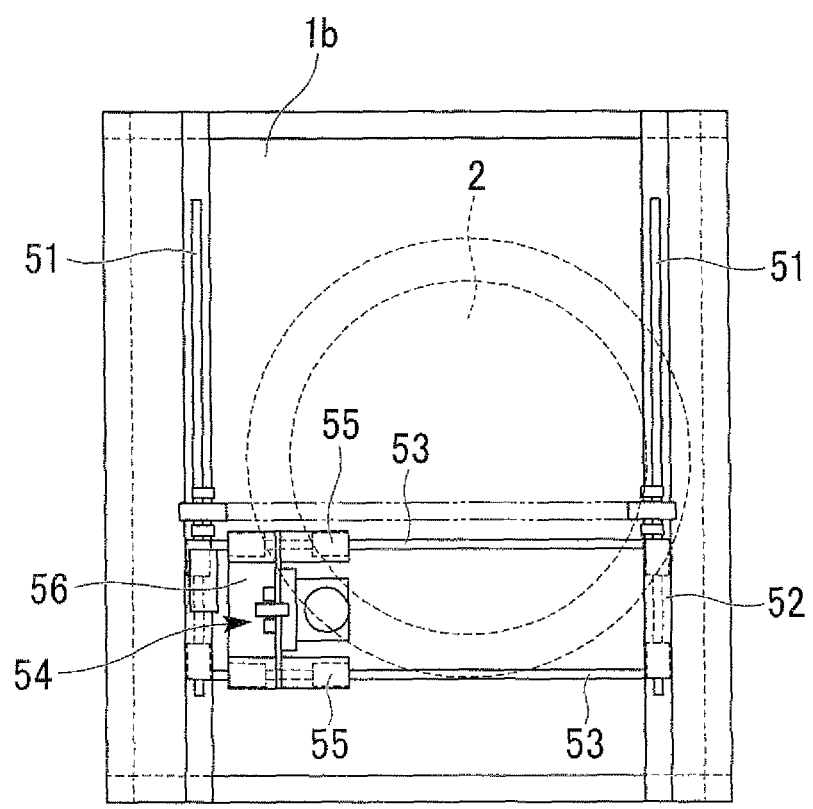
FIG. 8 is a schematic plan view showing an example of a glove box equipped with a robot of the present invention.
Figure 9:
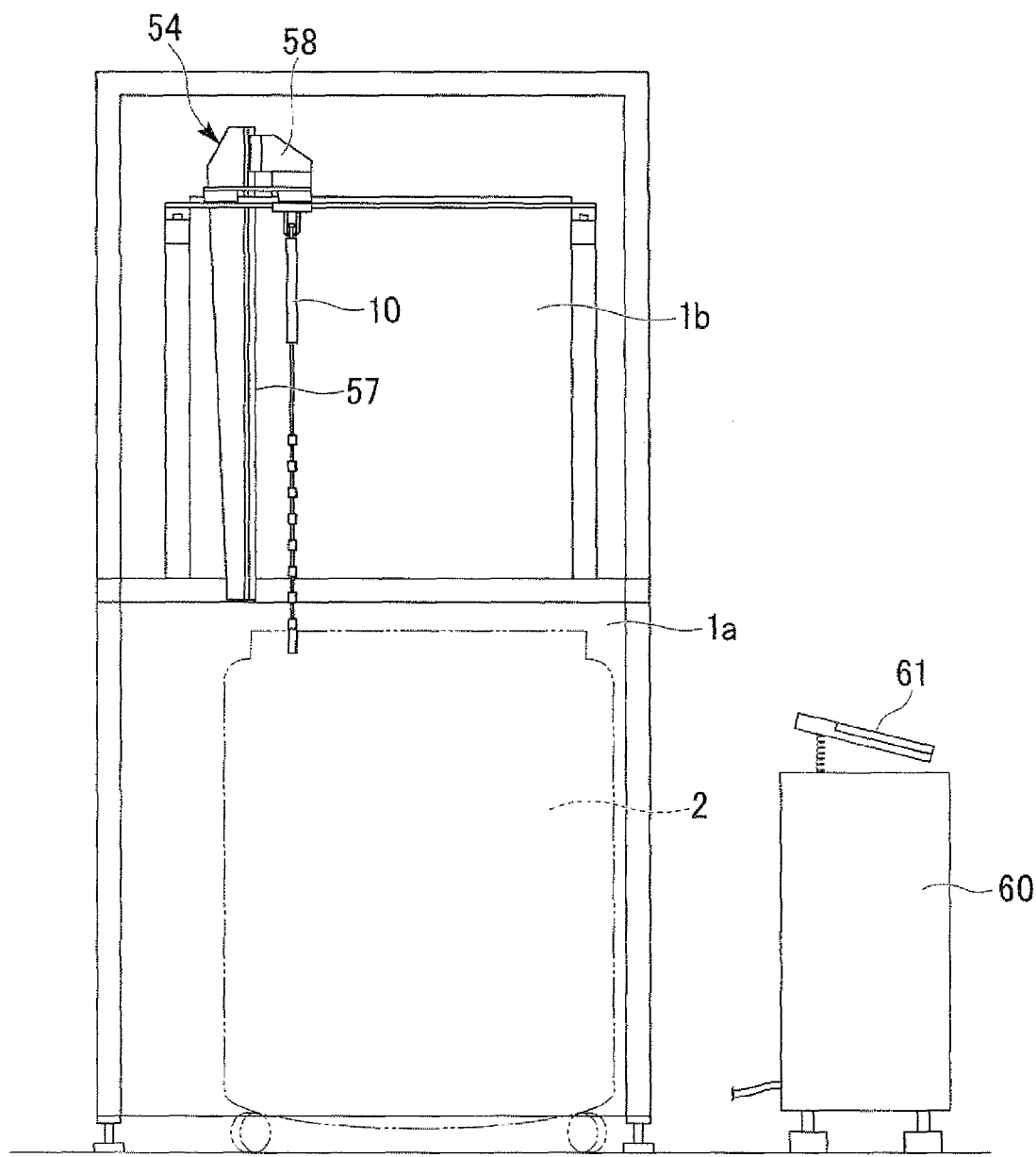
FIG. 9 is a schematic side view showing an example of the glove box equipped with the robot of the present invention.
Figure 10:
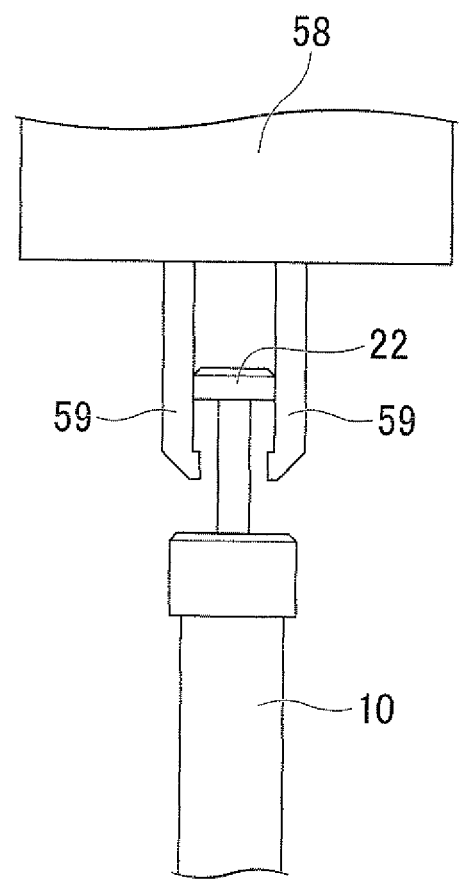
FIG. 10 is a schematic block diagram showing an example of the structure of the robot in the present invention.

FIGS. 8 to 10 show one example of a glove box equipped with an automatic handling robot. Here, the automatic handling robot (hereinafter refer to as a robot) is provided in the upper space of the work space section 1b.

A pair of parallel X-axis rails 51, 51 is attached to the upper portion of the work space section 1b as shown in FIG. 8. The X-axis rail 51 has a smooth round-bar shape for example, and those are respectively disposed at one end edge and the other end edge facing it of the ceiling wall.

A pair of X-axis trestles 52, 52 that each reciprocates the X-axis rail 51 is mounted to the X-axis rails 51, 51. This X-axis trestle 52 is a hollow cylindrical member, and the X-axis rail 51 passes through the hollow portion of the inside thereof, and the X-axis trestle 52 slides so as to reciprocate in the X-axis direction.

Two round-bar shaped Y-axis rails 53, 53 parallel to each other are bridged so as to connect the pair of X-axis trestles 52, 52. One Y-axis trestle 54 that reciprocate the pair of Y-axis rails 53, 53 is amounted to the pair of Y-axis rails 53, 53.

The Y-axis trestle 54 is comprised of a pair of sliding bodies 55, 55 and a coupling body 56 connecting the pair of sliding bodies 55, 55.

The sliding body 55 is comprised of a hollow cylindrical body, and the Y-axis rail 53 passes through the hollow portion of the inside thereof, and the sliding body 55 slides so as to reciprocate in the Y-axis direction. Thereby, the Y-axis trestle 54 as well reciprocates in the Y-axis direction.

As shown in FIG. 9, one Z-axis rail 57 is mounted to the Y-axis trestle 54 so as to droop. The Z-axis rail 57 is configured such that its leading end portion extends close to the partition board 1c. A gripper head 58 is mounted so as to be movable up and down to the Z-axis rail 57.

As shown in FIG. 10, a pair of gripping pieces 59, 59 for gripping the handle portion 22 of the ampoule storing tool 10 is provided to the lower surface of the gripper head 58.

The pair of gripping pieces 59, 59 are configured to come close to or be spaced from each other, thereby making it possible to grip or release the handle portion 22.

In this example, the shape of the handle portion 22 is preferably formed to be rectangular columnar, thereby, at the time of gripping the handle portion 22 by the gripping pieces 59, 59, the direction of the ampoule storing section 23 of the ampoule storing tool 10 is determined, and the direction is defined as the side of an operator. Further, reading of barcodes, and operations of taking-out and housing of ampoules are made easy.

With the above-described structure, the gripper head 58 is capable of freely moving in the three-axis directions that is the Y-axis direction, the Y-axis direction, and the Z-axis direction in the work space section, thereby it is possible to pull up an arbitrary one of the ampoule storing tools 10 housed in the cryopreservation vessel 2 up to an arbitrary position.

Such an operation of the gripper head 58 is to be controlled by a control apparatus 60 installed outside the glove box 1.

The operations of taking-out and mounting of an ampoule by the robot are performed as follows.

First, since the position of the cryopreservation vessel 2 in the housing section 1a is slightly shifted by taking in or out the cryopreservation vessel 2 in some cases, it is necessary to set a reference point (an original point) of the gripper head 58 in each case.

The setting of the reference point is performed by carrying out an operation for two to three of the ampoule storing tools 10, that a specified one of the ampoule storing tools 10 is pulled up to a predetermined position from the cryopreservation vessel 2, the gripping pieces 59, 59 of the gripper head 58 are moved to this position, to grip the handle portion 22 by the gripping pieces 59, 59, and the identification management number of the ampoule 25 or the ampoule storing section 23 exposed in this state is input to the control apparatus 60 to carry out teaching. The identification management number is input to the control apparatus 60 by use of an input apparatus 61 such as a graphic panel.

Further, there is a method for the setting as well that arbitrary reference points (two points) are provided to the upper surface of the cap 9 in advance with respect to the X-Y axis directions, and the positions of the respective ampoule storing tools 10 and the position of the reference points are stored as their positional relationships in the control apparatus 60 in advance, and in the case where the cryopreservation vessel 2 is shifted, the robot (which is visually confirmable by a laser light) is returned to the reference points by fine-tuned driving, to store it again. However, the setting is not limited these methods.

Note that, with respect to the Z-axis, it is possible to respond to a slight shift by making the portion under the neck of the handle portion 22 longer. However, the height of the cryopreservation vessel 2 is adjusted by a level adjuster mounted under foot of the vessel 2, which makes it possible to match the open and closed positions of the gripping pieces 59, 59 to the position of the handle portion 22.

At the time of taking out the ampoule 25, an identification management number of an ampoule to be brought out is input to the input apparatus 61. Thereby moving the gripper head 58 to a target position, and causing the gripping pieces 59, 59 to grip the handle portion 22 of the target ampoule storing tool 10, to pull up the ampoule storing tool 10 until the target ampoule 25 is exposed to the outside, and the gripper head 58 stops.

In this state, an operator inserts his/her hands into the gloves 6 of the work space section 1b, to manually take out the ampoule 25 from the ampoule storing tool 10, and houses it in the ampoule exit/entrance box 32, to take it out of the glove box 1.

Next, when a "take-out/put-in completion button" of the input apparatus 61 is pressed, the gripper head 58 pushes the ampoule storing tool 10 into the cryopreservation vessel 2 and opens the gripping pieces 59, 59, and returns to the waiting position.

At the time of housing an ampoule, in the same way as the time of taking out it, the target ampoule storing tool 10 is pulled up from the cryopreservation vessel 2, to expose the empty ampoule storing section 23 to be a target.

In this state, the operator manually houses the ampoule into the empty ampoule storing section 23.

Next, when the "take-out/put-in completion button" of the input apparatus 61 is pressed, the gripper head 58 pushes the ampoule storing tool 10 into the cryopreservation vessel and opens the gripping pieces 59, 59, and returns to the waiting position.

By use of such a robot, a work for visually confirming the first identification code of the ampoule storing tool 10 is no longer required at the time of pulling up the ampoule storing tool 10 to be a target from the cryopreservation vessel 2, which improves the working efficiency.

Since the approximately 300 to 500 ampoule storing tools 10 are inserted in the cryopreservation vessel 2, it takes time to carry out the visual confirmation work, which may bring about misidentification. However, such a disadvantage can be dissolved by use of this robot.

Another Embodiment of Glove Box Equipped with Automatic Handling Robot

Figure 11:
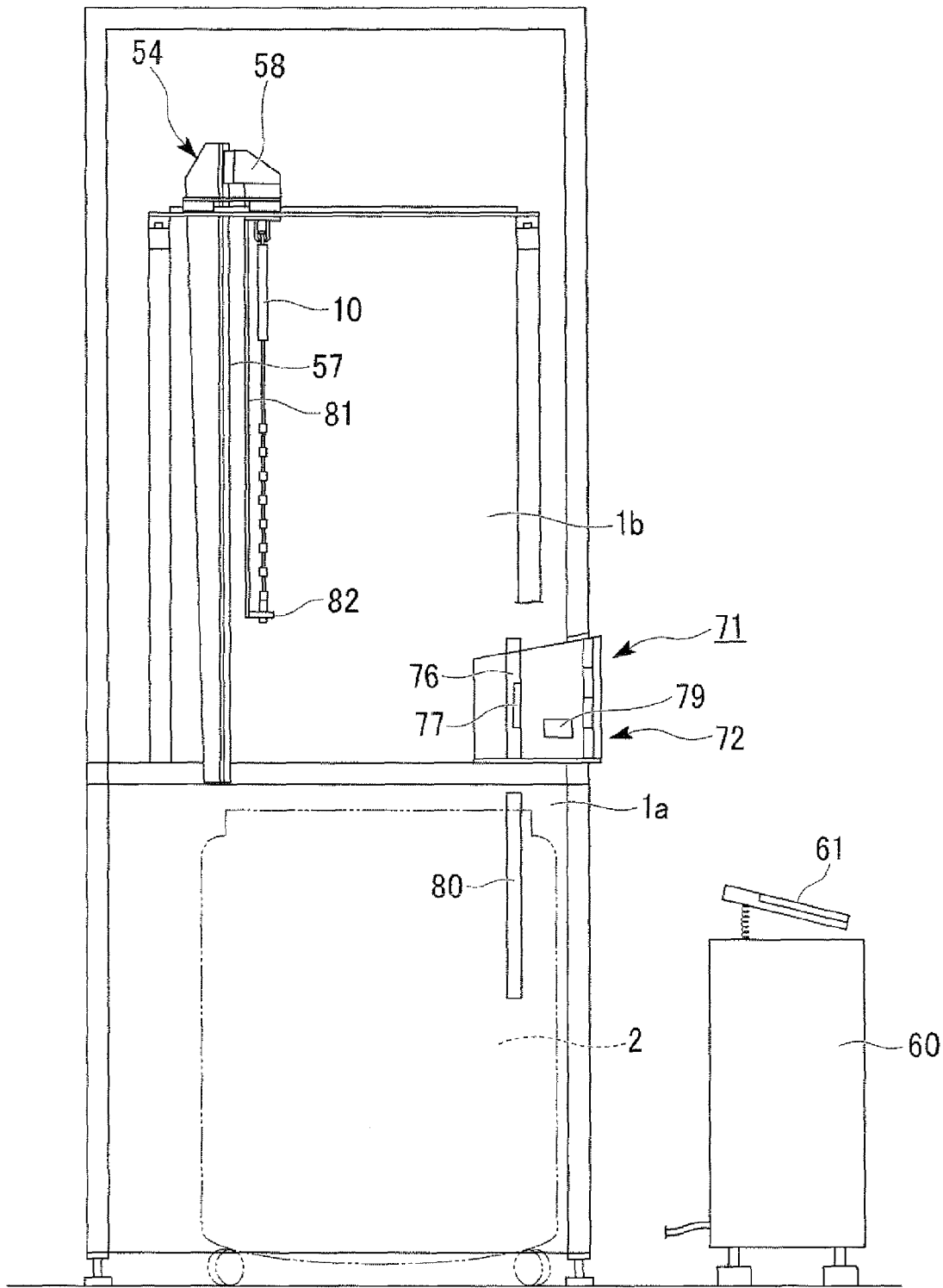
FIG. 11 is a schematic side view showing another example of the glove box equipped with the robot of the present invention.
Figure 12:
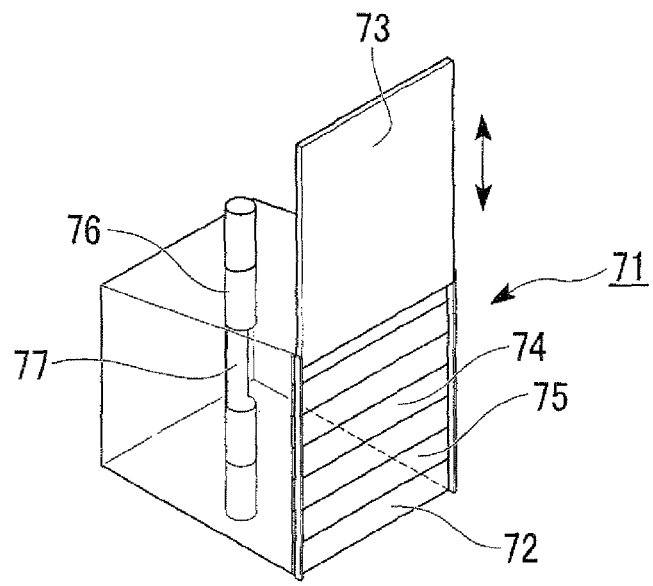
FIG. 12 is a schematic block diagram showing an example of a pass box in the present invention.
Figure 13:
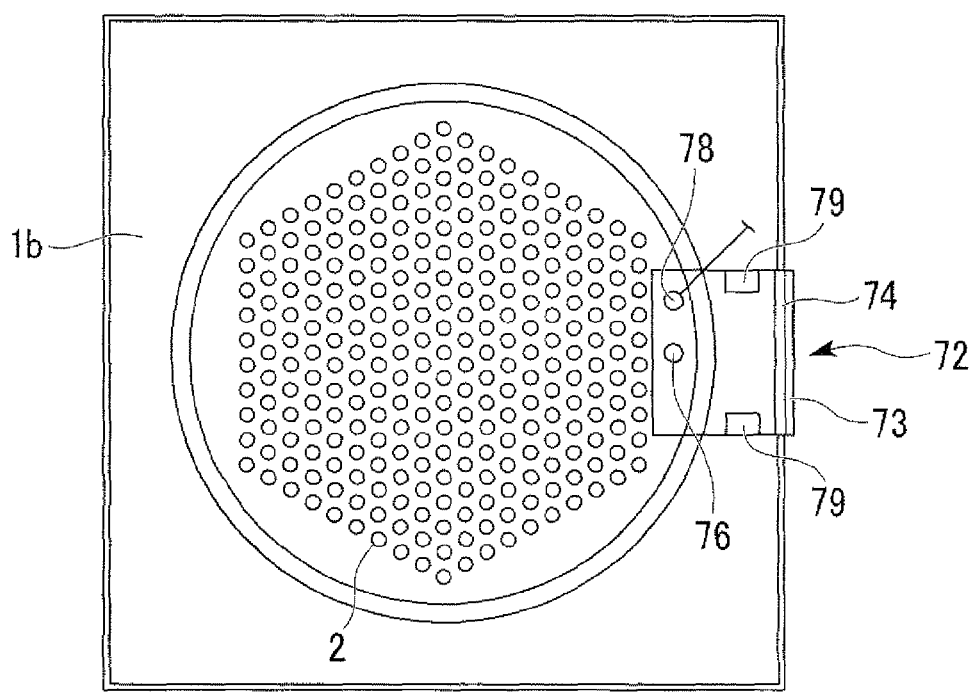
FIG. 13 is a schematic plan view showing another example of the glove box equipped with the robot of the present invention.

FIGS. 11 to 13 show another embodiment of the glove box equipped with the robot.

In this embodiment, a pass box 71 is provided in the vicinity of the partition board 1c in the putting-in/out work space section 1b. This pass box 71 is a substantially rectangular parallelepiped box body which has a hollow inside and is comprised of a transparent material such as glass, acrylic resin, or carbonate resin.

One side surface of the pass box 71 is exposed so as to face the outside from the opening portion formed so as to notch a part of the wall forming the work space section 1b, and this side surface is served as an operation port 72.

The operation port 72 must be always closed to be airtight, and is configured as shown in FIG. 12, to be usually closed with an outer door 73 comprised of a transparent plate material, and to show an inner door 74 by moving the outer door 73 upward or laterally as needed.

The inner door 74 is comprised of a plurality of flexible belts 75, 75 comprised of a material rich in flexibility such as a rubber or a flexile plastic foam being arrayed with no space in a vertical direction, and it is possible for an operator to insert his/her hands between the flexible belts 75, 75 to perform a work in the pass box 71. Note that the outer door 73 may be omitted by making an airtight structure of the inner door 74. Further, in FIG. 12, the longitudinal direction of the flexible belts 75, 75 is set to a horizontal direction. However, the direction may be another direction other than a horizontal direction. For example, the longitudinal direction of the flexible belts 75, 75 may be a vertical direction, and in this case, the flexible belts 75, 75 are arrayed with no space in a horizontal direction.

Further, an upper housing pipe 76 passing through from the upper surface to the lower surface thereof is provided in the pass box 71. The upper housing pipe 76 is a pipe into which the ampoule storing tool 10 pulled out of the cryopreservation vessel 2 by the robot is inserted.

As shown in FIG. 12, a takeoff port 77 is formed in the upper housing pipe 76. This takeoff port 77 is an opening portion for an operator to grip and take out the target ampoule 25 from the ampoule storing tool 10 when the ampoule storing tool 10 is inserted into the upper housing pipe 76, which is slightly greater than the size of the ampoule 25.

Moreover, as shown in FIG. 13, a discharge port 78 from which a dry gas with which the inside of the pass box 71 is filled to be at positive pressure at least in operation is discharged, is provided in the pass box 71, and this discharge port 78 is connected to the aforementioned dry gas supply tube 28 (refer to FIG. 3).

Fixed bar-code readers 79, 79 are provided by one on the both sides in the pass box 71. This bar-code reader 79 is for reading a bar-code of a bar-code label attached to the ampoule 25 to perform identification management of the ampoule 25, and bar-code information from the bar-code readers 79, 79 are to be input to the control apparatus 60.

Note that the bar-code reader 79 is not limited to be set in two, and may be one.

As shown in FIG. 11, a lower housing pipe 80 is provided in the cryopreservation vessel 2. This lower housing pipe 80 is a pipe for housing the lower portion of the ampoule storing tool 10 when the ampoule storing tool 10 pulled out by the robot is inserted into the upper housing pipe 76. However, depending on an inserted depth of the ampoule storing tool 10, the lower portion of the ampoule storing tool 10 is not housed in the lower housing pipe 80 in some cases.

The lower housing pipe 80 is provided so as to pass through the cap 9 of the cryopreservation vessel 2, to reach the inside of the inner vessel 12.

The planar position of the lower housing pipe 80 is set immediately beneath the upper housing pipe 76, thereby causing each of the ampoule storing tools 10 to be housed so as to pass through the upper housing pipe 76 and the lower housing pipe 80.

A bar shaped leg portion 81 extending downward is mounted to the Z-axis rail 57. This leg portion 81 is capable of moving up and down along the Z-axis rail 57. A through hole for the leg portion 81 is formed in the gripper head 58, which enables the gripper head 58 to move up and down along the Z-axis rail 57 and the leg portion 81. A clamp 82 for gripping the lower end portion of the ampoule storing tool 10 is provided to the lower end portion of the leg portion 81. The upper portion and the lower portion of the ampoule storing tool 10 pulled out of the cryopreservation vessel 2 are respectively gripped by the clamp 82 and the pair of gripping pieces 59, 59. Thereby preventing the ampoule storing tool 10 from sliding at the time of moving, which makes it easy to insert the ampoule storing tool 10 into the upper housing pipe 76. Note that, in the case where the gripper head 58 comes close to the place above the cap 9 in order to pull out the ampoule storing tool 10, the leg portion 81 comes down to the lower end of the Z-axis rail 57 and the clamp 82 opens, not to interrupt the operation of the gripping pieces 59, 59 of the gripper head 58.

The leg portion 81 is not limited to the above-described example, and may be directly mounted to the gripper head 58. In this case, the shape of the leg portion 81 is formed into a shape which is extensible. Thereby, in the case where the gripper head 58 comes close to the place above the cap 9 in order to pull out the ampoule storing tool 10, the leg portion 81 shrinks above the cap 9 and the clamp 82 opens, not to interrupt the operation of the gripping pieces 59, 59 of the gripper head 58.

Further, the clamp 82 may be directly mounted to the Z-axis rail 57. In this case, the clamp 82 is made movable up and down along the Z-axis rail 57. Thereby, in the case where the gripper head 58 comes close to the place above the cap 9 in order to pull out the ampoule storing tool 10, the clamp 82 comes down to the lower end of the Z-axis rail 57 and opens, not to interrupt the operation of the gripping pieces 59, 59 of the gripper head 58.

Further, a program for executing the following operations is built in the control apparatus 60.

That is, the program is for executing a series of operations in which, when an identification management number of an ampoule is input to the input apparatus 61, the gripper head 58 pulls out the target ampoule storing tool 10 to hold its lower portion with the clamp 82, and moves the ampoule storing tool 10 in this state up to the place immediately above the upper housing pipe 76, and moreover, the gripper head 58 inserts the ampoule storing tool 10 into the upper housing pipe 76 or the upper housing pipe 76 and the lower housing pipe 80, and stops when the target ampoule 25 comes to the position of the takeoff port 77.

In this embodiment, bar-code labels on which information such as their identification management numbers and the like are recorded are pasted onto the body portions of all the ampoules 25 (not shown). Further, in this embodiment, the gloves 6, 6, and the ampoule exit/entrance boxes 32, 32 are no longer required.

Hereinafter, the operations in this embodiment will be described.

When an identification management number of an ampoule to be brought out is input to the input apparatus 61, the control apparatus 60 executes the aforementioned program, the gripper head 58 of the robot pulls out the ampoule storing tool 10 from the cryopreservation vessel, the lower portion of the ampoule storing tool 10 is held with the clamp 82, and the ampoule storing tool 10 in this state is moved up to the position immediately above the upper housing pipe 76 of the pass box 71.

Next, the ampoule storing tool 10 is inserted into the upper housing pipe 76, and when a target ampoule among the plurality of ampoules housed in the ampoule storing tool 10 descends down to the position of the takeoff port 77 of the upper housing pipe 76, the insertion of the ampoule storing tool 10 is stopped. At this time, the ampoule 25 housed in the ampoule storing tool 10 is to face the takeoff port 77.

At this time, the two bar-code readers 79, 79 read a bar-code of the ampoule exposed through the takeoff port 77, to transmit its identification management number to the control apparatus 60.

In the control apparatus 60, the identification management number from the bar-code readers 79, 79 and the identification management number from the input apparatus 61 are compared, and in the case where the both are matched to one another, it is confirmed that the ampoule is the target ampoule, that is indicated by an indicator lamp, an indicator buzzer, or the like.

The operator opens the outer door 73 of the pass box 71 after confining this indication, and inserts his/her hands into the inside through the operation port 72 from the inner door 74, to take out the ampoule.

Next, when the "take-out/put-in completion button" of the input apparatus 61 is pressed, the gripper head 58 pulls out the ampoule storing tool 10 from the upper housing pipe 76, to insert the ampoule storing tool 10 into the original position of the cryopreservation vessel 2, which terminates the putting-out work.

Note that, when the ampoule storing tool 10 is inserted into the original position of the cryopreservation vessel 2, or inserted into the upper housing pipe 76, since the shapes of the lower portion of the thermal insulating section 21 of the ampoule storing tool 10 and the lower portion of the guide pipe 24 are formed into tapered shapes so as to become thinner than the respective body portions (not shown), it is possible to insert the ampoule storing tool 10 more smoothly.

When an ampoule is stored in the ampoule storing tool 10, in the same way as taking-out of an ampoule, the target ampoule storing tool 10 is pulled up from the cryopreservation vessel 2, to be inserted into the upper housing pipe 76, and the empty ampoule storing section 23 to be a target is exposed through the takeoff port 77.

In this state, the operator manually houses the ampoule into the ampoule storing section 23 via the operation port 72 of the pass box 71.

At this time, the bar-code readers 79, 79 read the bar-code attached to the ampoule to transmits the identification management number to the control apparatus 60, the identification management number is compared with the identification management number input to the input apparatus 61, and it is confirmed whether or not the target ampoule is housed in the target ampoule storing section 23. When the operator knows the fact confirmed by an indication as described above, the operator presses the "take-out/put-in completion button" of the input apparatus 61.

Then, the gripper head 58 of the robot pulls out the ampoule storing tool 10 from the upper housing pipe 76, and inserts the ampoule storing tool 10 into the original position of the cryopreservation vessel 2, which terminates the putting-in work, and the gripper head 58 returns to the waiting position.

In this embodiment, it is possible to bring the atmosphere in the pass box 71 into in a dry state, and frost does not adhere to the ampoule exposed through the takeoff port 77 in any case. Therefore, the bar-code attached to the ampoule is certainly and unmistakably read by the bar-code readers 79, 79. Therefore, it is possible to precisely confirm that the ampoule taken out of the ampoule storing tool 10 or housed in the ampoule storing tool 10 is the target one, which makes it possible to prevent confusing of ampoules.

Further, a significant part of the ampoule putting-in/out work, in particular, a work for specifying an ampoule is automatically performed, which greatly reduces a load on an operator.

Moreover, in the case where an ampoule to be a target is housed in the ampoule storing section 23 in the upper portion of the ampoule storing tool 10, since a great part of the ampoule storing tool 10 is located in the lower housing pipe 80 of the cryopreservation vessel 2, the ampoule existing in this portion is kept in a cooling state. Therefore, the frequency of applying wasteful heat to the ampoule is reduced.

(Modification of Glove Box Equipped with Automatic Handling Robot)

Figure 14:
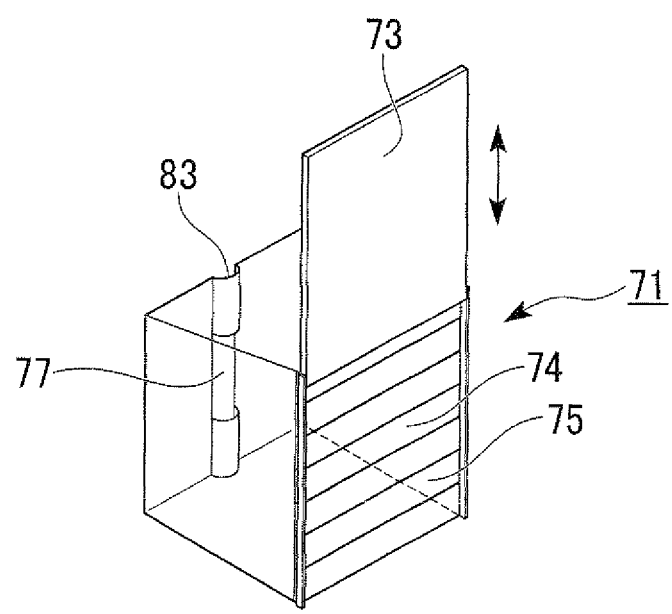
FIG. 14 is a schematic block diagram showing another example of the pass box in the present invention.

FIG. 14 shows a main part of a modification of the aforementioned embodiment.

In this modification, the upper housing pipe 76 is not provided in the pass box 71, and a longitudinal groove portion 83 is provided in the back surface of the pass box 71 in place of the upper housing pipe 76. This longitudinal groove portion 83 whose cross sectional shape is a semi-circular shape, is formed so as to be along the vertical direction in the back surface of the pass box 71. The takeoff port 77 is formed in the intermediate portion thereof so as to notch the portion. This takeoff port 77 is for taking out an ampoule therethrough in the same way as in the previous example.

In this modification, the ampoule storing tool 10 pulled out of the cryopreservation vessel 2 is configured to descend down so as to be along the longitudinal groove portion 83, and a target ampoule is taken out of or housed into through the takeoff port 77.

In the above-described embodiment, the pass box 71 is disposed in the central portion of one side surface of the putting-in/out work space section 1b in view of its operability. However, the pass box 71 is not limited thereto, and may be disposed in the corner portion of the pass box 71. However, in the glove box 1, it is impossible to provide the lower housing pipe 80 at the inside of the cryopreservation vessel 2 in some cases, or the lower housing pipe 80 may be not necessarily provided in some cases. Therefore, the lower portion of the ampoule storing tool 10 inserted into the upper housing pipe 76 of the pass box 1 is to be always exposed to room temperature.

INDUSTRIAL APPLICABILITY

According to the present invention, it is possible to store a variety of biological samples for a long period and stably in respective research institutes and medical institutions in the biomedical field, medical field, pharmaceutical field, and livestock field.

The invention claimed is:

1. A cryopreservation vessel comprising:
a vessel body which holds a low-temperature liquefied gas;
a cap which closes an opening section of the vessel body and has a plurality of through holes that are formed so as to pass through in a vertical direction;
sheath tubes, each including a hollow portion disposed in one of the through holes of the cap; and
ampoule storing tools which are housed so as to be able to pass through the hollow portions of the sheath tubes, wherein a plurality of gas permeable holes are formed in each of the sheath tubes, and
the ampoule storing tools are each comprised of a support pillar and a plurality of ampoule storing sections which are equipped with the support pillar so as to be arrayed in a vertical direction of the support pillar.

2. The cryopreservation vessel according to claim 1, wherein the ampoule storing tools comprises a thermal insulating section provided in the upper portion of the support pillar.

3. A glove box comprising:
a housing section which houses the cryopreservation vessel according to claim 1; and
a putting-in/out work space section which is provided so as to be communicated with an upper portion of the housing section, wherein
the putting-in/out work space section is transparently visible from outside, and is filled a dry gas to be at positive pressure, and
a putting-in/out work for an ampoule storing tool of the cryopreservation vessel housed in the housing section is performed inside the putting-in/out space section.

4. The glove box according to claim 3, wherein
a dew point meter for measuring a dew point in the putting-in/out work space section is provided, and
a dry gas supply section, which supplies a dry gas for lowering the dew point in the space section into the putting-in/out work space section in the case where a value indicated by the dew point meter shows a predetermined value or more, is provided.

5. The glove box according to claim 3, wherein
an automatic handling robot, which pulls up a specified ampoule storing tool from the cryopreservation vessel, and next pushes the specified ampoule storing tool, is provided at a ceiling portion of the putting-in/out work space section.

6. The glove box according to claim 5, wherein
the automatic handling robot operates by three-axial control based on instructions on a position of a specified ampoule storing tool and a position of an ampoule stored in the ampoule storing tool.

7. The glove box according to claim 6, wherein
the automatic handling robot is equipped with a gripper head, and
the gripper head travels in three-axis directions to move to a position of a specified ampoule storing tool, pulls up the ampoule storing tool until a specified ampoule is exposed from the cryopreservation vessel, and next pushes the ampoule storing tool.

8. The glove box according to claim 5, wherein
a pass box is provided to the putting-in/out work space section,
the pass box has an airtight operation port that opens outside, and has an upper housing pipe into which an ampoule storing tool pulled up from the cryopreservation vessel by the automatic handling robot is inserted, and
a takeoff port for taking out an ampoule from the inserted ampoule storing tool is formed in the upper housing pipe.

9. The glove box according to claim 8, wherein
the pass box is made of a transparent material, and an inside of the pass box is filled with a dry gas.

10. The glove box according to claim 8, wherein
a bar-code is put on the ampoule, and the ampoule of the ampoule storing tool taken out by the automatic handling robot is identified on the basis of identification management information of the bar-code.

11. The glove box according to claim 5, wherein
a pass box is provided to the putting-in/out work space section,
the pass box has an airtight operation port that opens outside, and has a back surface in which a longitudinal groove portion is formed such that an ampoule storing tool pulled up from the cryopreservation vessel by the automatic handling robot is set along the longitudinal groove portion, and
a takeoff port for taking out an ampoule from the inserted ampoule storing tool is formed in the longitudinal groove portion.

12. The glove box according to claim 11, wherein
the pass box is made of a transparent material, and an inside of the pass box is filled with a dry gas.

13. The glove box according to claim 11, wherein a barcode is put on the ampoule, and the ampoule of the ampoule storing tool taken out by the automatic handling robot is identified on a basis of identification management information of the bar-code.

14. The glove box according to claim 3, wherein
a tube line for supplying a liquefied gas to the cryopreservation vessel is provided, and
the tube line passes through the housing section and the cryopreservation vessel, and one end of the tube line extends to a bottom portion of the cryopreservation vessel and the other end is connected to a liquefied gas supplier.

15. A cryopreservation vessel comprising:
a vessel body which holds a low-temperature liquefied gas;
a cap which closes an opening section of the vessel body and has a plurality of through holes that are formed so as to pass through in a vertical direction;
sheath tubes, each including a portion disposed so as to extend through an interior of one of the through holes of the cap; and
ampoule storing tools configured to pass through the portions of the sheath tubes,
wherein:
a plurality of gas permeable holes are formed in each of the sheath tubes, and
the ampoule storing tools are each comprised of a support pillar and a plurality of ampoule storing sections which are equipped with the support pillar so as to be arrayed in a vertical direction of the support pillar.

16. The cryopreservation vessel according to claim 15, wherein the ampoule storing tools are configured to be inserted into the vessel body via passage through the portions of the sheath tubes.

17. The cryopreservation vessel according to claim 16, wherein the portion of each sheath tube has a hollow configuration to receive therein one of the ampoule storing tools.

18. The cryopreservation vessel according to claim 15, wherein the ampoule storing tools comprises a thermal insulating section provided in the upper portion of the support pillar.

19. A glove box comprising:
a housing section which houses the cryopreservation vessel according to claim 15; and
a putting-in/out work space section which is provided so as to be communicated with an upper portion of the housing section, wherein
the putting-in/out work space section is transparently visible from outside, and is filled a dry gas to be at positive pressure, and
a putting-in/out work for an ampoule storing tool of the cryopreservation vessel housed in the housing section is performed inside the putting-in/out space section.

20. The glove box according to claim 19, wherein
a dew point meter for measuring a dew point in the putting-in/out work space section is provided, and
a dry gas supply section, which supplies a dry gas for lowering the dew point in the space section into the putting-in/out work space section in the case where a value indicated by the dew point meter shows a predetermined value or more, is provided.

\* \* \* \* \*